US009763757B2

(12) United States Patent
Llop et al.

(10) Patent No.: US 9,763,757 B2
(45) Date of Patent: Sep. 19, 2017

(54) METHOD FOR CREATING A VIRTUAL ORAL-MAXILLOFACIAL ANATOMICAL REPRESENTATION

(71) Applicants: Daniel R Llop, Reno, NV (US); Armand C. Jusuf, Reno, NV (US)

(72) Inventors: Daniel R Llop, Reno, NV (US); Armand C. Jusuf, Reno, NV (US)

(73) Assignee: NATIONAL DENTEX, LLC, Palm Beach Gardens, FL (US)

( * ) Notice: Subject to any disclaimer, the term of this patent is extended or adjusted under 35 U.S.C. 154(b) by 70 days.

(21) Appl. No.: 14/522,558

(22) Filed: Oct. 23, 2014

(65) Prior Publication Data
US 2015/0327958 A1    Nov. 19, 2015

Related U.S. Application Data

(60) Provisional application No. 62/000,075, filed on May 19, 2014.

(51) Int. Cl.
| | | |
|---|---|---|
| *A61C 9/00* | (2006.01) | |
| *A61C 13/00* | (2006.01) | |
| *A61C 13/34* | (2006.01) | |
| *A61C 1/08* | (2006.01) | |

(52) U.S. Cl.
CPC ............ *A61C 9/0053* (2013.01); *A61C 9/004* (2013.01); *A61C 13/0004* (2013.01); *A61C 1/084* (2013.01); *A61C 13/34* (2013.01); *A61C 2201/005* (2013.01)

(58) Field of Classification Search
CPC ... A61C 9/0053; A61C 9/004; A61C 13/0004; A61C 13/34; A61C 1/084; A61C 2201/005
USPC .......................................... 433/213, 214, 72
See application file for complete search history.

(56) References Cited

U.S. PATENT DOCUMENTS

| | | | |
|---|---|---|---|
| 6,671,539 B2 | 12/2003 | Gateno et al. | |
| 8,371,849 B2 | 2/2013 | Gao | |
| 8,543,234 B2 | 9/2013 | Gao | |
| 2007/0190481 A1* | 8/2007 | Schmitt | A61C 13/0004 433/68 |
| 2011/0060558 A1* | 3/2011 | Pettersson | A61B 17/8685 703/1 |
| 2012/0100500 A1* | 4/2012 | Gao | A61C 1/084 433/72 |
| 2012/0214121 A1* | 8/2012 | Greenberg | A61B 5/0088 433/24 |

(Continued)

*Primary Examiner* — Michael Carey
(74) *Attorney, Agent, or Firm* — Baker & McKenzie LLP

(57) ABSTRACT

The invention could be a process for creating a dental anatomical representation comprising the following steps, seating radiopaque elastomer material between an upper jaw and a lower jaw of a mouth of a patient, the patient then fully biting down upon the radiopaque elastomer material to form the radiopaque elastomer material into a physical record of at least a portion of each of the two jaws and each jaw's position relative to the other jaw; taking a first scan of the patient's mouth with the formed radiopaque elastomer material in place between the jaws; and creating a virtual representation of the formed radiopaque elastomer material from data presented in the first scan, then using the virtual representation to align and correlate data obtained from the first scan and any other scans of a patient's anatomy.

20 Claims, 7 Drawing Sheets

(56) References Cited

U.S. PATENT DOCUMENTS

2013/0249907 A1 9/2013 Humphries et al.
2015/0064644 A1 3/2015 Scherer

* cited by examiner

METHOD FOR CREATING A VIRTUAL ORAL-MAXILLOFACIAL ANATOMICAL REPRESENTATION

STATEMENT REGARDING FEDERALLY SPONSORED RESEARCH OR DEVELOPMENT

Not Applicable

REFERENCE TO A "MICROFICHE APPENDIX"

Not Applicable.

FIELD OF THE INVENTION

The present invention may relate to those methods and processes used in scanning technologies for obtaining digital databases that can be used for the development of maps and models of true patient specific oral-maxillofacial anatomy. More specifically, the present invention may be related to those methods and processes used in scanning technologies for obtaining digital databases that can be used for the development of virtual representation of true patient specific oral-maxillofacial anatomy that do not utilize fiduciary markers, radiographic templates or shape of known dimensions (SKD) to integrate multiple sets of data obtained from various kinds of scanners.

BACKGROUND

The digital age can be seen as starting a revolution in the dental field and how dental care can be provided to the patient. Digital processing and scanning technologies are generally allowing the dental practitioner to use a variety of scanning and computing technologies to supplant and/or supersede older technologies for measuring and recording an architecture of a patient's mouth; making virtual and physical models of the patient's mouth; making dental diagnoses; creating dental surgical plans; and manufacturing various dental accoutrements such as implants, prosthetics, abutments, surgical guides and other such dental devices. The current anatomical representation science and methods could be seen as being further capable of diagnosing and providing guidance in treatment planning for almost every oral-maxillofacial surgical procedure by presenting to the dental health care provider with an anatomical representation or simulation that accurately represents the true patient's anatomy. As dental digital capability becomes more economically affordable and practical, these dental services and materials, which were originally only provided only by dental labs, can now be provided by the dental practitioners' offices in less time and with lower costs.

The science behind providing true and accurate patient specific anatomical representation could be seen as comprising of an alignment, correlation, and validation of multiple sets of digital data captured by object acquisition (e.g., scanning) machines such as intra-oral optical or laser scanners, 3D optical scanners, 3D laser scanners, medical CT scanners, CBCT (i.e., Cone Beam Computed Tomography) scanners and the like. However, with so many dental digital anatomical scanning and representation capabilities or modalities (e.g., scanning devices/scanning device data processing means) that are now available to the dental field, the differences in the attributes of these various scanning and representation capabilities, individually and cumulatively, could contribute factors that may otherwise lead to inaccuracies occurring in the created anatomical representations, dental guidance and dental diagnoses unless there was a coordinating or unifying means that can be used with these capabilities.

For example, although commonly used in oral-maxillofacial treatment planning, the scan-based anatomical reconstruction method may often be ignored in lieu of simple cast fitting process. One possible reason for this preference could be that the scan-based anatomical reconstruction method could be seen as introducing possible errors into the anatomical representation capability because the scan-based anatomical reconstruction method may be subject to a dental technician's perspective on what is the thought to the best alignment of the representation of the captured portions of the jaws (e.g., bites, arches, or alike.) In this manner, the scan-based anatomical reconstruction method could substantially require a dental technician to subjectively correlate and align a higher quality detail laser or optical scan of the patient's intra-oral anatomy to lower-quality detail of the same anatomy (e.g., tooth structure) as generally provided by a CBCT (e.g., Cone Beam Computed Tomography) scan. CBCT scans are generally being seen being used for primarily capturing data regarding patient's mouth bone anatomy (e.g., cortical and trabecular.) Additionally, it could be hard to objectively identify useful dental anatomies that are not readily visible in the CBCT scans such as soft tissues, scattered data, and other objects observed in other non-CBCT scans.

Another possible limitation to the CBCT scanning is that many CBCT scanned patients (e.g., adult patients) may have existing dental metal in their mouth such as crowns, bridges, implants, etc., which can cause distortions to occur in large amounts of recorded CBCT scan data making the scanned intra-oral anatomy details unusable relative to dental planning and anatomical representation purposes. These distortions, which may be known as "scatter", may occur when the CBCT scanner's conal x-ray beam projection into the patient's mouth hits the dental metal, which may cause the x-rays to ricochet or "scatter" in unwanted directions preventing the CBCT scanner from accurately recording the projected x-ray reflection.

Yet another limitation present in many dental scanning modalities may not accurately present an accurate representation of the true patient anatomy because these scanning modalities use only a minimal amount of data processing because only one set of scanned data is used (e.g., many times in dental planning, this is the obtained volumetric data or only that data obtained by external and artificial scan appliances and not is fully cross-referenced with other data sets as provided by another scanning device.) Patient's anatomies as reconstructed using such minimalistic scanning modalities or other such means may often discard or otherwise discount into the anatomical representation consideration a significant amount of filtered CBCT scatter data. This inability to properly process, integrate and filter the CBCT scatter data may further inhibit the proper alignment of secondary anatomy data such as dental casting model within other sets of scan data obtained from the patient.

Therefore dental practitioners using current scanning modalities may find it hard to consistently and reliably obtain a true and accurate patient-specific anatomical representation (and resulting the dental guidance and diagnose based on such anatomical representation). As a result, dental surgical and restorative treatment planning in the oral-maxillofacial environment have been continually challenged with the inaccuracies often associated with misalignment, non-representative anatomical simulation, and erroneous correlation of scan data by the attempted using of fiduciary marker-based scanning appliances to otherwise coordinate the various sets of dental digital data.

Such fiduciary marker-based scanning appliances could include a bite tray that has embedded radiopaque material (e.g., little balls of x-ray reflecting material such as titanium) having known measured qualities (e.g., size, placement, and the like) that can be inputted into the DICOM (i.e., Digital Imaging and Communications in Medicine software standards) scanning data processing system. The bite tray (with bite registration material that is not radiopaque) could inserted in the mouth of the patient, the patient then bites down on the bite registration material, and during the scan, the scanning device can "see" the radiopaque fiduciary markers of the bite tray. The fiduciary marker-based scanning appliance's known measurements can be used with the DICOM scan data processing system to help coordinate the integration, alignment, overlay and alike of scan data from multiple scanning sources by identify common reference or coordination points between various scan data sets.

The fiduciary marker-based scanning appliances may have their own scanning distorting influence that may significantly inhibit the obtained scan data from being fully orchestrating into a true patient specific virtual representation. Furthermore, fiduciary marker-based scanning appliances may present an overall inability to quantitatively calculated to what extent inaccuracies have occurred in created anatomical representations because there is substantially no one way to measure and quantify, universally and empirically, over the combined scans (due to varying detail quality), variances in scan systems themselves, and various scatter/distortion generation produced by the scans.

Further, fiduciary marker-based scanning appliances in order to be useful generally need to meet three qualifications or factors in order to maintain accuracy in such scanning modalities: 1) the fiduciary marker-based scanning appliance should be perfectly fitted in the patient's anatomy; 2) The fiduciary markers used in such an scanning appliance should be found to be perfectly consistent within both the patient scan and the scan of the fiduciary marker-based scanning appliance; and 3) the scanning appliance itself (e.g., the appliance frame) must not flex. As to the first factor, generally, a perfect fitting may be nearly impossible because many times these fiduciary marker based scanning appliances can be too rigid and awkward in size to easily conform to a patient's intra-oral environment.

The second factor may be arguably difficult to maintain as well in that various CBCT, laser, or optical scanners produce non-uniform, different quality scans. As a result, the portion of scan recording the radiographic fiduciary markers may have variances in the measurements of radiopaque fiduciary markers (e.g., the scans could show the radiopaque fiduciary markers as varying in size) as an output function of a particular scan. For example: a one type of scan could measure and report that 3 mm sized radiopaque fiduciary markers as being more or less that the actual 3 mm size of the radiopaque fiduciary markers. The reported radiopaque fiduciary marker measurement variance may occur because of the scan ambient environment, the scan system's inherent quality, and the possibility of distortion due to metallic surrounding scatter. These fiduciary marker measurement variances could result in inconsistent or improper matchup of the markers resulting in overall mis-matchup inaccuracies within the scan sets of data as processing by the scanning modality. Though such variances could be combated by increasing the number of scan markers throughout a scan, one can easily argue that more scan markers do not necessarily mean more accuracy but merely more chances for error.

For the third factor, when a scan appliance is in a patient's mouth and is bit down upon, the resilience of the radiographic fiduciary scanning appliance can temporarily flex within the patient's mouth instead of substantially conforming to the patient's dental anatomy. Once the scanning appliance is subsequently removed from the patient's mouth to be scanned, the scan appliance will revert or flex back to its original form, which will be different from the way the scan appliance was scanned in the patient's mouth leading to further possible inaccuracies.

These contributing error factors individually, cumulatively, and otherwise could introduce serious inaccuracies to the various scan(s) data sets with resulting compilation having unwanted inaccuracies.

What is needed therefore is new key or means to coordinate the various dental scan technologies and properly integrate the resulting sets of scan data in a manner that limits the possible of the occurrence of the inaccuracies as mention above. One possible solution to these inaccuracy issues could be the present invention, which may be a new method to substantially allow more accurate and true digital or virtual representation of patient specific anatomies by generally enhancing the capability of correlation between a various types of scanning modalities (e.g., CBCT scan, medical CT scan, laser scans, optical scans and the like.) The present method or process may use a bite registration means that lacks fiduciary markers, radiographic templates or shape of known dimensions (SKD) and yet generally provides a universal and consistent matchup or coordination means between various scanning modalities or capabilities. The present invention's scanning matchup or coordination method substantially provides a significantly consistent and identical matchup between the relationship and morphology of a higher detail quality scan with the relationship and morphology of the lower detail quality scans.

The invention could use a radiopaque elastomer or polymer material (e.g., a vinyl polysiloxane with 85 Shore A Durometer attributes) as a bite registration material without the use of other artificial and non-anatomical mouth structures such a bit tray, radiographic fiduciary markers and the like. When the patient bits down upon the radiopaque elastomer or polymer material placed between the jaws (e.g., placed between the alveolar ridges or dental arches) for a scan of the patient's mouth, the scanning modality during the scan can "see" and record the formed radiopaque elastomer material with the other data for that scan. That data from that subsequently created scan file can then be used and manipulated by DICOM dental software so that the formed radiopaque elastomer material can then be recognized and isolated as a structure separate from the patient's scanned anatomy. The DICOM software using the formed radiopaque elastomer material image/data can then integrate the various other scan data/images to form patient-specific virtual model of the scanned portions of the patient's anatomy.

The invention in this manner can be seen as substantially meeting three key requirements for data correlation between scanning modalities namely: 1) providing a coordination key that fits perfectly within the patient's anatomy—the bite registration material constantly and accurately meets and captures the relationship between the maxillary and mandibular occlusion (e.g., the patient's bite and its relationship to the jaw joint); 2) providing a coordinating key constantly retains the same read measurements for various scans taken of the patient in that the formed radiopaque elastomer material substantially captures dental detail (e.g., teeth) that may be consequently matched to various anatomical landmarks provided by other scans; and 3) the formed radiopaque elastomer material consistently conforms to the patient's anatomy without resistance and does not revert to pre-scan formation after removed from the patient's mouth post scan to substantially avoid the rigidity issues imposed by conventional scan trays.

In this manner, the present invention can be seen as using a formed radiopaque elastomer material to form a bit registration that can be used a coordination key to correlate patient CT scan data, dental casts or laser scans of intra-oral anatomy or optical scans of intra-oral anatomy to create true inter-arch relationship definition, accurate anatomical matching, and data merging. The present invention can be seen as generally eliminating the need to use a dental technician's artistic capabilities to substantially correct those errors/inaccuracies that may occur when combining the results of high definition scanning modalities with the results of low definition scanning modalities to generally create the anatomical representation.

SUMMARY OF ONE EMBODIMENT OF THE INVENTION

Advantages of One or More Embodiments of the Present Invention

The various embodiments of the present invention may, but do not necessarily, achieve one or more of the following advantages:

the ability to substantially limit the amount of inaccuracies that can occur when utilizing multiple scanning data sets to create an true and accurate representation of a portion or more of a patient's anatomy;

provide a coordinating scanning data key that could be based on a scanned combined upper and lower bit impression taken in complete occlusion;

the ability to use a lower and upper bit full occlusion impression to generally connect an upper and lower dental casting that may be subsequently scanned for incorporation with other scans;

provide coordinating scanning data key that may be based on a scanned combined upper and lower bit impression taken in complete occlusion that can subsequently be used to generally filter out scatter or other scan background noise when a plurality of scans are being used to create a patients anatomical representation;

the ability to scan a full occlusion formed bite registration material having a radiopaque ingredient to allow the full occlusion formed bite registration material to be substantially properly read and recorded by a dental scanning means;

provide a virtual representation of formed radiopaque elastomer material that is used to eliminate scatter effect and background noise from data obtained from the dental scans of a patient's anatomy for the formation of the virtual representation of the scanned portion of the patient's anatomy;

the ability to use a virtual representation of the formed radiopaque elastomer material to prevent scan distortions and scattered data from being incorporated into a scan-based formation of an anatomical representation of a scanned portion of the patient's mouth; and provide a virtual representation of the formed radiopaque elastomer material to check teeth-to-teeth and tissue-to- tissue alignments of any dental scans being used to form the virtual representation of the scanned portion of the patient's anatomy.

These and other advantages may be realized by reference to the remaining portions of the specification, claims, and abstract.

Brief Description of One Embodiment of the Present Invention

One possible embodiment of the invention could be a process for creating a dental anatomical representation comprising the following steps, but not necessarily in the order shown, seating only a radiopaque elastomer material between an upper jaw and a lower jaw of a mouth of a patient, the patient then fully biting down upon the radiopaque elastomer material to form the radiopaque elastomer material into a physical record of at least a portion of each of the two jaws and each jaw's position relative to the other jaw when the jaws are in the full occlusion position; taking a first scan of the patient's mouth with the formed radiopaque elastomer material in place between the jaws, the patient's mouth being at the full occlusion position; and creating a virtual representation of the formed radiopaque elastomer material from data presented in the first scan, then using the virtual representation of the formed radiopaque elastomer material to align and correlate data obtained from the first scan and any other scans of a patient's anatomy for a formation of a virtual representation of the scanned portion of the patient's anatomy.

Another possible embodiment of the invention could be a method of filtering scan data to create an anatomical representation of a patient's mouth comprising of the following steps, but not necessarily in the order shown, seating a radiopaque elastomer material between the jaws of a patient's mouth with the patient biting down upon the radiopaque elastomer material to form the radiopaque elastomer material into a physical record of at least a portion of each of the patient's jaws and the jaws' positions relative to one other when at the full occlusion position; taking a first scan of the patient's mouth with the formed radiopaque elastomer material between the jaws of the patient's mouth at the full occlusion position; taking a second scan that is different from the first scan; using data generated by the first and second scans to create a virtual representation of the formed radiopaque elastomer material; and using the virtual representation of the formed radiopaque elastomer material to align and correlate the first and second scans and any other scans used to form a virtual representation of the scanned portion of the patient's anatomy.

The above description sets forth, rather broadly, a summary of one embodiment of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

DESCRIPTION OF CERTAIN EMBODIMENTS OF THE PRESENT INVENTION

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

Figure 1:
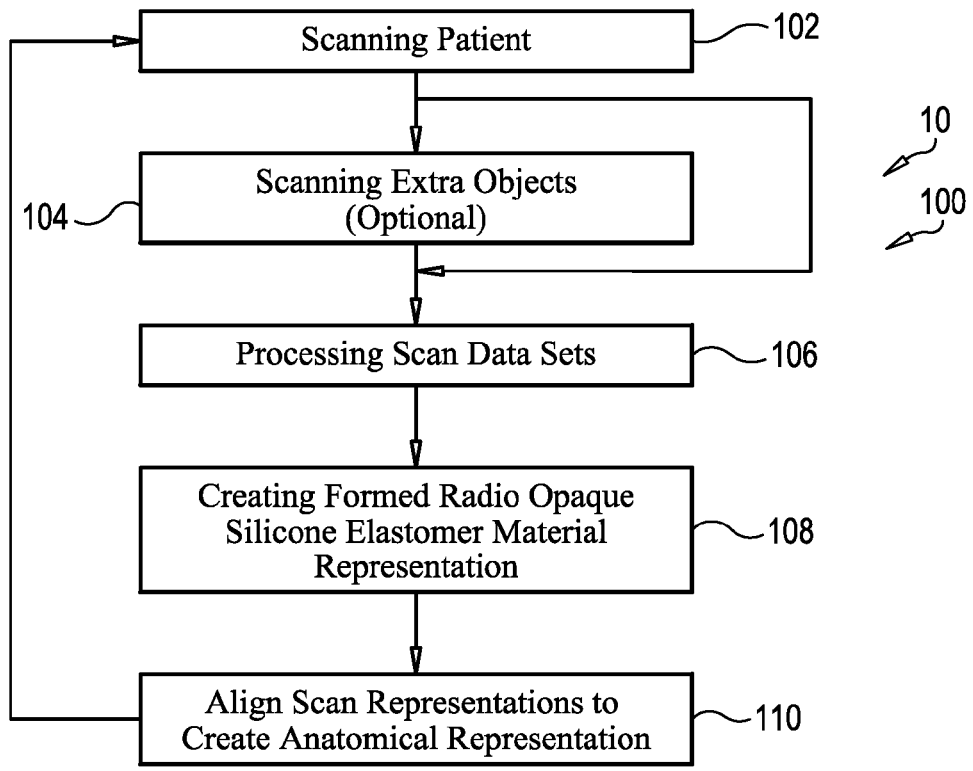
FIG. 1 is substantially showing a flow chart schematic for one embodiment of the method of the present invention.

As substantially shown in FIG. 1, the present invention 10 could comprise a method or process 100 for generally properly aligning, coordinating and correlating an assembly of data sets provided by a variety of scanning modalities (e.g., patient scan, digitized patient impression or cast-model poured from mold via laser or optical scanning, and digitized direct patient scan of intra-oral anatomy, etc.) to create true patient-specific anatomy representation without the use of artificial radiographical trays, dental appliances, markers and the like. The invention 10 in this manner could present dental and medical professionals with a true and accurate digital or virtual visualization of a patient's anatomy with many real-life elements such as critical neurological landmarks, vascular anatomies, high detail teeth representation, surrounding tissue detail, and true captured inter-arch relationship. It should be noted that dental arches could generally mean the crescent arrangements of teeth, with each crescent arraignment being located on each respective jaw (e.g., one crescent arraignment on an upper jaw or maxillae and the other crescent arrangement located on a lower jaw or mandible.) In cases of severe tooth loss, the dental arch could generally further comprise of the jaw area where the lost tooth (or lost teeth) were originally located or should have been located on the respective jaw. In a true edentulous (e.g., toothless) patient mouth environment, the alveolar ridges (e.g., portions of the jaw line generally defining the sockets of the teeth or where the teeth sockets should be located) could be captured and measured.

The invention 10 may also be used to aid the physical fabrication of rapid prototyped model displaying patient-specific true dental anatomies capable of including critical neurological landmarks, vascular anatomies, high detail teeth representation, surrounding tissue detail, and true captured inter-arch relationship. The invention 10 may be able to substantially remove a various inaccuracies provided by scanning modalities to allow the utilization of the virtual or the physical final anatomical representation having sufficient quality, clarity and accuracy to allow such a representation to be used to complement oral-maxillofacial surgical and restorative procedures, including but not limited to, dental implants, bone grafting, sinus lifting, enamelplasty, orthodontics, extractions, full-mouth bridge fabrication, and oral-maxillofacial "resecting." The data integrating capability of the invention 10 may allow resulting physical or virtual anatomical representation to be used in the manufacture of various surgical and treatment guidance appliances for the specific oral-maxillofacial treatment procedure, including but not limited to, dental implant, maxillectomies, mandibulectomy, bone reduction, bone grafting, superficial implant positioning (chin, orbital, etc.), and teeth preparations. The invention 10 may be used in conjunction with other technologies to produce dental guide appliances that can be various and diverse oral-maxillofacial treatment procedures.

Yet another embodiment for the invention 10 could be an utilization of the method in nearly any present patient condition, so as long as the radiopaque elastomer material (e.g., vinyl polysiloxane or other suitable silicon-based elastomer) can be applied on any anatomical surfaces. The embodiment may accommodate any of the following combination of patient oral conditions, but are not limited to, partially dentate scenarios whereby the patient exhibits some teeth in one or both arches; fully edentulous conditions whereby the patient exhibits no teeth on one or both arches, as well as patient currently wears or not wearing prosthetic appliances. When applied, the invention 10 may allow for proper and accurate representation of patient anatomy in any virtual or physical environment. It is important to note that fiduciary markers attached to dentures for fully edentulous cases or even partially edentulous scenarios may no be longer necessary as long as invention protocols are substantially followed.

The radiopaque elastomer material that could be used to form bite registration in at least one embodiment of the invention 10 could be a radiopaque silicone elastomer material formed from polyvinylsiloxane (e.g., vinyl polysiloxane) with radiopaque materials added to it. In one possible embodiment, the inventors have generally determined that the polyvinyl siloxane (referred to as PVS henceforth) and also known as poly-vinyl siloxane, vinyl polysiloxane, or vinylpolysiloxane, generally in 85 Shore A Durometer quality (e.g., a measurement on a hardness scale for rubber and rubber-like products) could providing proper scan visibility qualities (e.g., being radiopaque) when used with the various scanning modalities. The viscosity of this material may also allow for the solidifying of the bite registration material into an elemental state that may be similar to that of rubber. The viscosity and elemental state of this material may allow the material to form around the shape of object to which is it is applied. The material may then solidify to substantially form a rubberized and excellent impression record of the surrounding intra-oral anatomies, more specifically the crown-level detail of teeth and oral tissue.

Additionally, PVS is generally radiopaque. This physical property may allow for more clarity in the scan of the bite registration material to assist in identifying dental occlusal morphology and relationship against the opposing oral structure (or its scan-based representation.) Again, as a result, artificially fabricated (that is fabrication not "naturally"

shaped by true dental anatomies) generally cannot match the conformity and visibility that could be provided by the present invention using the described method and materials.

An example of this radiopaque silicon-based elastomer material is sold under the US trademark BLU-MOUSSE® by Parkell Inc., 300 Executive Dr, Edgewood, N.Y. 11717.

Figure 2:
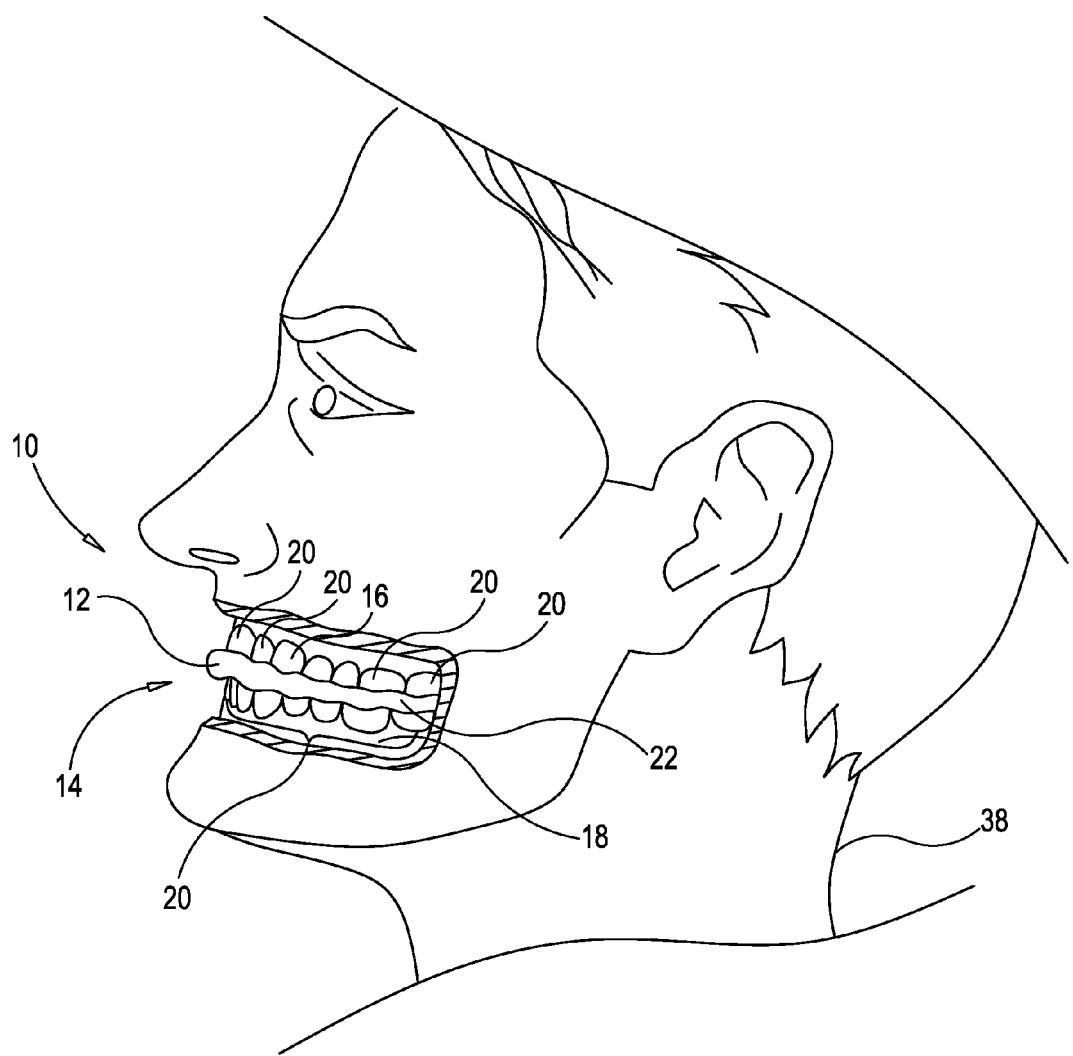
FIG. 2 is substantially showing a perspective cutaway view of the bite registration material as placed in a patient's mouth.
Figure 3:
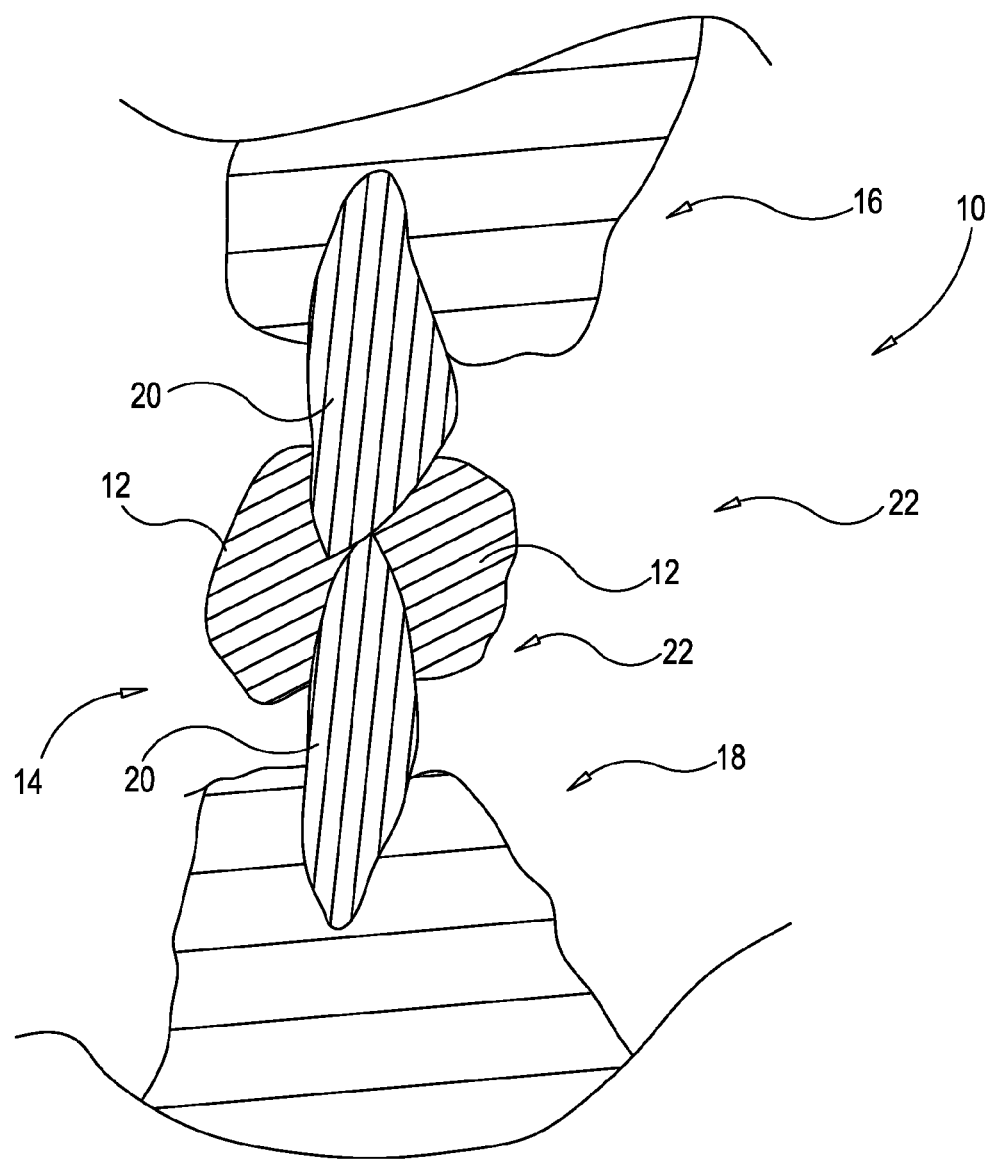
FIG. 3 is substantially showing a side elevation cutaway view of the bite registration material as placed in a patient's mouth.
Figure 3A:
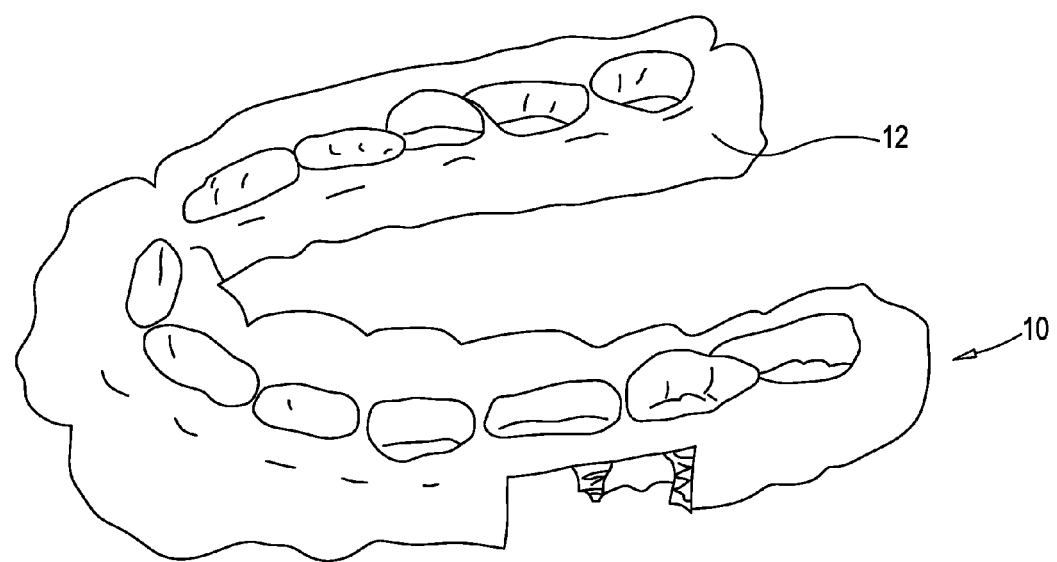
FIG. 3A is substantially showing a perspective cutaway view of the bite registration material as formed and removed from the patient's mouth.

As substantially shown in FIG. 1, the method or process 100 of the invention 10 could start with step 102 scanning the patient. In this step, as substantially shown in FIGS. 2 and 3, the radiopaque elastomer material 12 could be stretched and formed in a basic cylindrical form and placed in the patient's open mouth 14 generally between the upper jaw 16 (e.g., upper arch) and lower jaw 18 (e.g., lower arch) with enough material to generally cover 33% of each single tooth 20 (or in some cases with tooth loss, covering the top [teeth portion] of denture located within the patient's mouth or gum portion where the teeth were formerly located) The radiopaque elastomer material 12 could be initially located upon the patient's lower bite (e.g., dental arch) 18 with the patient closing his (or her) teeth 20 upon the radiopaque silicone elastomer material 12 to form the combined lower and upper full occasional impression 22. One or more different types of scans could then be taken of the patient with the radiopaque silicone elastomer material 12 still clenched within the patient's mouth 14 at maximum intercuspation (i.e., the occlusal or closed position of the jaw wherein the cusps [raised points] of the teeth of both arches (e.g., bites) 16, 18 are fully interposed with the cusps of the teeth of the opposing jaws 16, 18.) As substantially shown in FIG. 3A, once the radiopaque elastomer material 12 has set (e.g. reached a rubberized solidified state) the patient 22 opens his or her mouth so the dental professional can remove the finalized and formed radiopaque elastomer material impression 22. The radiopaque silicone elastomer material impression 22 while in the patient's mouth is generally is used without a separate structural support (e.g., a bite tray), fiduciary markers, radiographic templates or shape of known dimensions (SKD).

As required, various other scans can be taken of the patient's mouth without the use of radiopaque silicone elastomer material to appropriately add to the scan database. The data set(s) created by the patient scan(s) can then be saved in a data file for further processing. As this step is substantially completed, in one process 100 can in one possible embodiment could proceed to optional step 104, scanning of extra oral objects or it could proceed to step 106, processing of the scan data sets.

In optional step 104, scanning of extra oral objects, dental impressions could be taken of the patient's mouth. As substantially shown in FIG. 4, an impression procedure could comprise of a bite tray with suitable bite registration material could be placed upon a bite of the patient mouth and the patient bites down upon the bite registration material. As substantially shown in FIG. 4, when the bit registration material solidifies (e.g., reaches a rubberized state) the tray/bite registration material 24 is removed from the patient's bite to reveal an analogue dental impression (e.g., a mold) of that bite. The impression process is then repeated for the patient's opposing bite.

Figure 4:
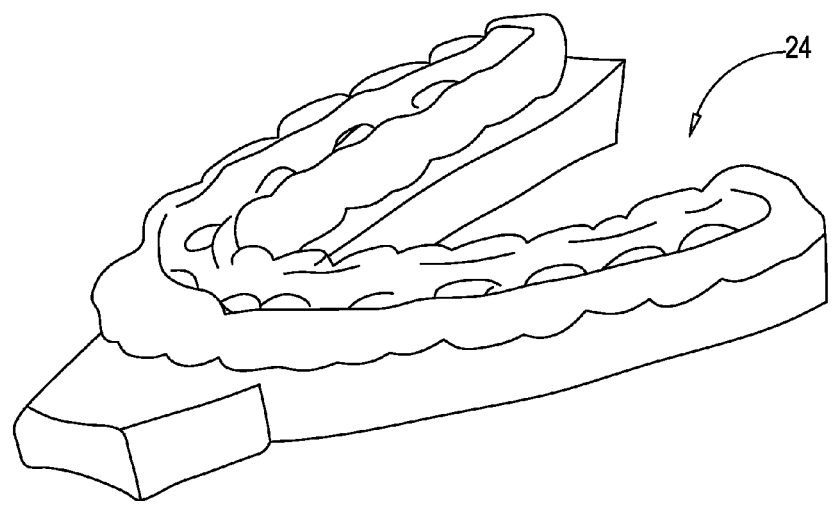
FIG. 4 is substantially showing a perspective view of an impression made of an arch of the patient's mouth.
Figure 4A:
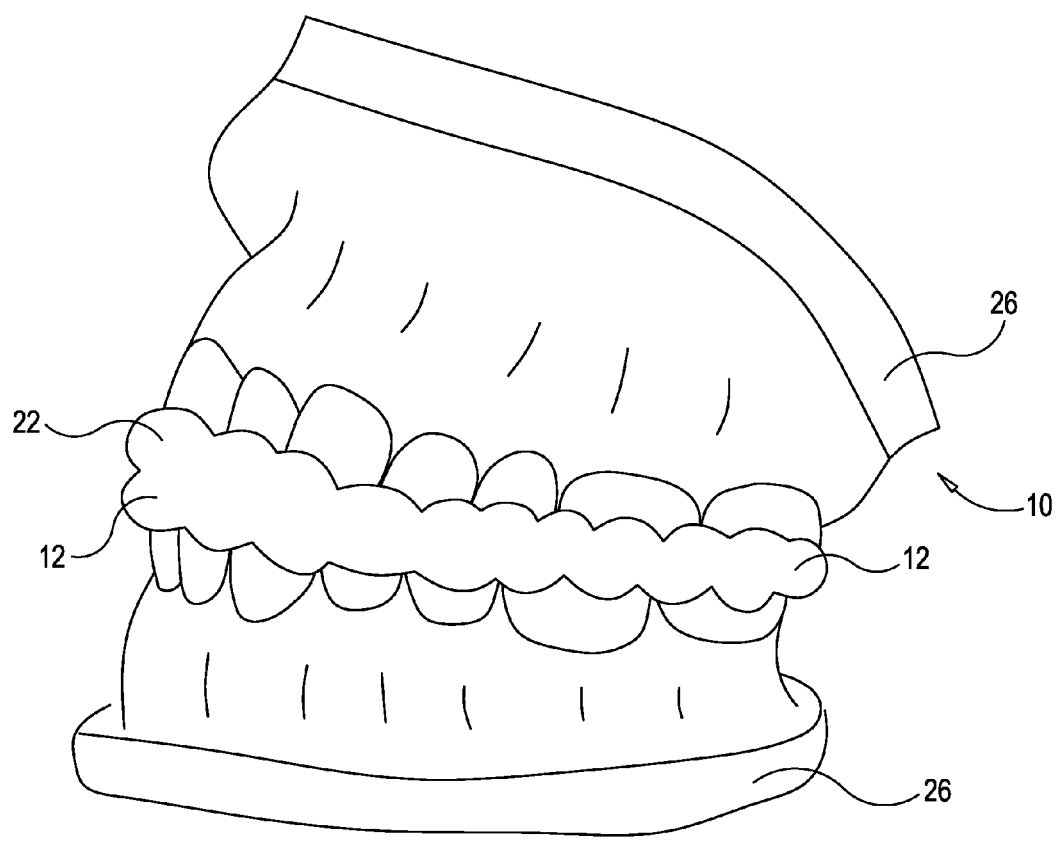
FIG. 4A is substantially showing a perspective view of the formed bite registration material as being placed between the upper and low bite castings of the patient's mouth.

As needed, as substantially shown in FIG. 4, dental casts may be for scanning as well. Dental casts could made from the dental impression(s) by pouring casting stone material into a formed dental impression (not shown) of the patient's mouth. When the dental casting stone material hardens, it forms a dental casting 26 or physical representation or true scale model of each respective arch. If two dental casts 26 are made (e.g., upper and lower arches), they are removed from their respective impressions and placed in an articulator, the resulting may form a solid working model of the patient's mouth.

The formed radiopaque silicone elastomer material or impression 22 made by the patient biting down upon the radiopaque silicone elastomer material 12, may then be placed between the arches of two bites castings (sans articulator) to ensure that the bite castings are so orientated in the same manner their real counterparts of the patients; mouth when full occluded. This combination of casting and formed radiopaque silicone elastomer material could then be suitably scanned together to form another scan data set for use in the invention 10. A series of different types of scans may be made of this combination.

By not using scan appliances (e.g., bite trays, scan templates, associated fiduciary markers and the like), the proper occlusal relationship presented by the dental castings 26 can now be identified in that a template or scan appliance that could if used could otherwise brace open the arch to some extent during a scan. This would prevent a true and accurate "bite down" or occlusal rendering or perspective creating a false condylar (e.g., jaw joint) positioning relationship for the resulting anatomical representation (could give rise to an overall wrong bite or arch alignment.) When the resulting anatomical representation is used in restorative dental planning, this inaccurately shown relationship between the arches could consequently result in inaccurate presentation of esthetic and function of the subsequently-created prosthetics.

In another embodiment, the dental impressions themselves (without the formed radiopaque elastomer material) may be scanned to add to the data set. The data of the scanned objects can be saved in their own separate file for further processing. As optional step 104 is substantially completed, the process 100 could proceed to step 106, processing of scan data sets.

In step 106, processing of scan data sets, DICOM standard (e.g., Digital Imaging and Communications in Medicine) imaging software (e.g., software used for handling, storing, printing, and transmitting information in medical imaging) can be used to process the sets of scan data from various scans. Due to these standards, the scan data itself cannot be altered, rather the process builds visual representations form each scan data set. These visual representations can then be aligned, coordinated and combined by the DICOM imaging software and operator intervention to form an overall (e.g., combined overlay) of the visual representations to form a patient specific and true anatomical representation of the patient's anatomy.

The imaging software can be loaded upon and run upon a suitable computer hardware system with appropriate operating software and operator interface capability. For over a decade in both the medical and dental fields, DICOM imaging software has be used to apply DICOM imaging sequencing to the scan data sets produced by the different scanning modalities used in those fields. DICOM Software with image sequencing capability such as Mimics provided by Materialise 590 Lincoln Street, Waltham, Mass. 02451, and the like have allowed dental and medical professionals to isolate and objectively identify certain anatomies accurately found in scans (e.g., CBCT scans.) As step 106 is substantially completed, the process 100 could proceed onto Step 108, isolating the formed radiopaque silicone elastomer material.

In step 108, isolating the formed radiopaque silicone elastomer material, the formed radiopaque silicone elastomer material can be differentiated from other structures in the patient's mouth/castings scans (e.g., various scan data files) through 3D pixel or density differentiation—the bite registration material having a different scanned density than the scanned teeth, gums, hard tissue of the patient) and can so be isolated from other scanned structures as a distinct and a separate object. Through the image segmentation, the formed radiopaque silicone elastomer material can be marked or denoted as being a separate object. This identification of the formed radiopaque silicone elastomer material into a formed radiopaque silicone elastomer material representation. This formed radiopaque silicone elastomer material representation can then be manipulated by the imaging software to check and coordinate the combining of the various scan results/representations of the patient's bite contours, interarch relationship of the patient's mouth and alike. As step 108 is substantially completed, the process 100 could proceed to step 110, aligning and matching various scans of the dental casts.

Step 110, aligning and matching of multiple scans, the various scans taken in the process can be aligned, matched up and overlaid through the DICOM image processing software. In doing so, the scans of the patient's mouth could be aligned together while optionally, the scans of the extra oral object (if taken) could be aligned together. Then the two combined sets of scans (patients mouth, extra oral object) could be aligned together to form the anatomical representation.

In the alignment of the various scan representations, the maxillary arch and mandibular arch teeth anatomies of the "overlaid" teeth contours of the scan representations could be align up to focus the overlaying of the scan representations in exact same respective positions for these scans. Visible and recognizable components of the optional dental cast scans could include clearly defined teeth and tissue contours along with the formed radiopaque silicone elastomer material. Further alignment between the scans can be accomplished by matching true teeth-to-teeth, tissue-to-tissue, and bite registration-to-bite registration using the formed radiopaque silicone elastomer material representation. The formed radiopaque silicone elastomer material representation during this immediate step could serve to illuminate and define the boundaries of teeth-to-teeth scan alignment and tissue-to-tissue scan alignment so that anything exceeding the parameters as denoted by the formed radiopaque silicone elastomer material representation could be properly and accurately be identified as not being a proper representation of the patient's true anatomy. The formed radiopaque silicone elastomer material representation can then be used in this processing to properly identify scan distortions, scattered data and the like. Once properly identified, the scan distortions, scattered data and the like can be discounted or eliminated from the formation of the anatomical representation of the scanned portion(s) of the patient mouth/patient's mouth representation (e.g., dental cast.)

Figure 4B:
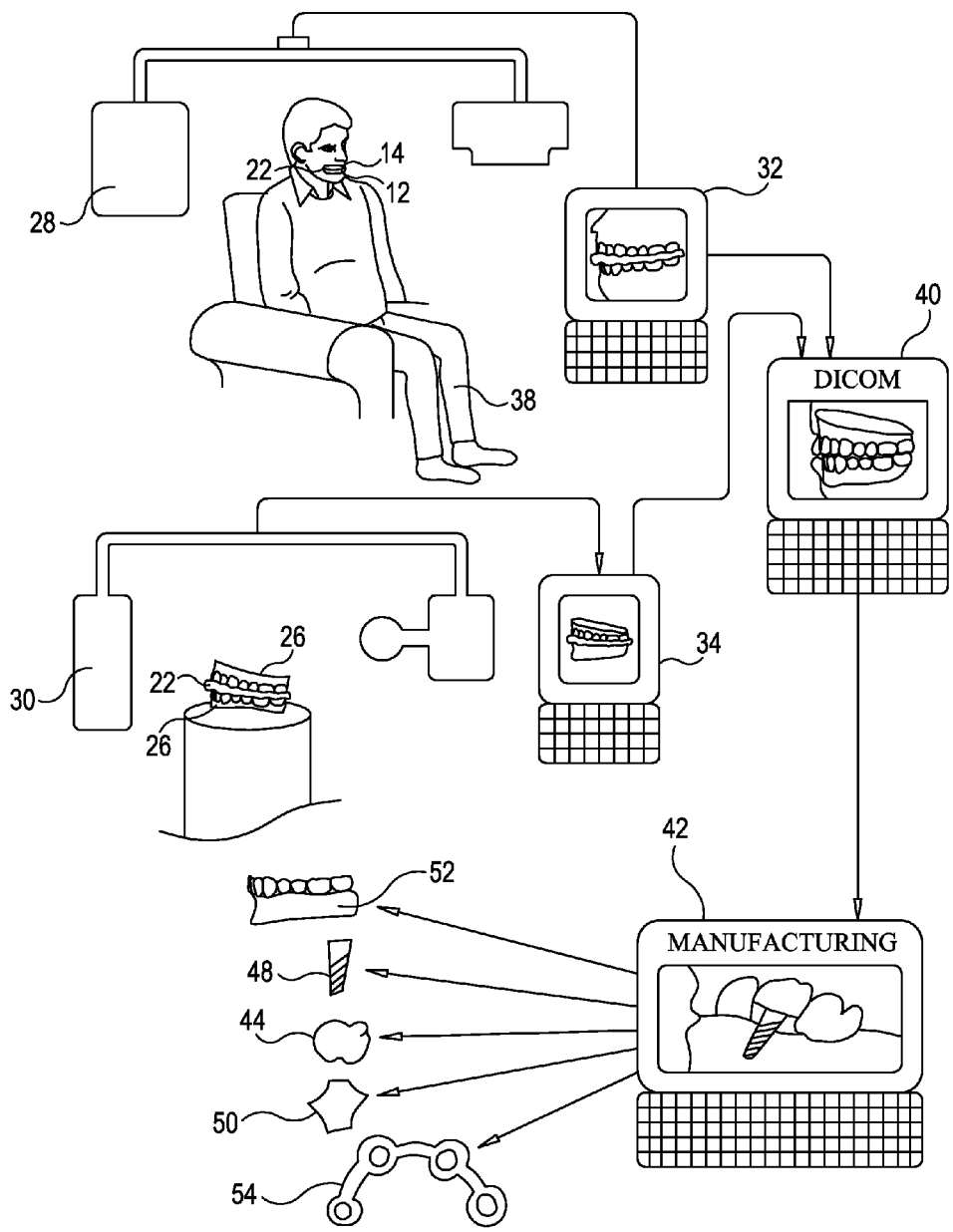
FIG. 4B is substantially shown a perspective schematic of a possible scanning network utilizing the invention.

As substantially shown, in FIG. 4B, one possible scanning network that could use the invention 10 could have a first type of scanner 28 (such as CBCT scanner) in which the patient 38 bites down on the radiopaque elastomer material placed in the patient's mouth 14 in a manner that makes an impression 22 of upper and lower jaw in full occlusion. The first scanner 28 could be connected to the first scanner computer 32 which could makes a file of the completed first scan.

The second scanner 30 could be a scanner different from the first scanner. The subject matter for the second scanner 30 could be a combination (e.g., located outside of the patient's mouth) in which dental castings previously made of the patient's mouth have the previously formed radiographic elastomeric material impression 22 of the patient's mouth placed between the two dental castings to help hold the two dental castings in the full occlusion position. This combination 56 could then be scanned by the second scanner and a file of the second scan could be made by the second scanner's computer 34. The respective scanning computers 32 and 34 could send their respective scan files to the DICOM computer system 40.

The DICOM computer system 40 with image separation capacity can be used with the sets of obtained scan data to substantially align and correlate data obtained from the scans, to generally identify and reduce error possibly introduced by the scan data to generally create a more accurate virtual representation of the patient's true anatomy. In combination with computer-guided design, planning manufacturing systems 42, the virtual representation can then be used to design and make a real the dental accoutrements (real dental models 52, implants 48, abutments 50, prostheses 44, dental surgical guides 54 and alike) as well as creating dental surgical procedures, plans and operations; and be part as well of an ever widening digital integration in the dental, medical and veterinarian fields.

CONCLUSION

Although the description above contains many specifications, these should not be construed as limiting the scope of the invention but as merely providing illustrations of some of the presently preferred embodiments of this invention. Thus, the scope of the invention should be determined by the appended claims and their legal equivalents rather than by the examples given.

As described, claimed and illustrated, the invention may scan a radiographic elastomer material placed between the jaws of a patient that are subsequently placed in a full occlusion position. The radiographic elastomer material can then so form an impression of portions of both jaws as well as record the jaw joint relationship of the two jaws. A DICOM computing system can then isolate the data as generally formed scan of the impression to create a virtual representation of the impression. This virtual representation of the impression can then subsequently be used to align and correlate data sets (e.g., virtual representations) of other dental scans in a manner that may identify and reduce the occurrence of error that might otherwise occur in combining the dental scans together for the creating of a virtual representation of patient's mouth.

What is claimed is:

1. A process for creating a dental anatomical representation comprising the following steps, but not necessarily in the order shown:

(A) seating only a radiopaque elastomer material between an upper jaw and a lower jaw of a mouth of a patient, the patient then biting down only upon the radiopaque elastomer material to form the radiopaque elastomer material into a physical record of at least a portion of each of the two jaws and each jaw's position relative to the other jaw when the jaws are in the full occlusion position;

(B) taking a first scan of the patient's mouth with the formed radiopaque elastomer material in place between the jaws, the patient's mouth being at the full occlusion position; and (C) creating a virtual representation of the formed radiopaque elastomer material from the results of the first scan, then using the virtual representation of the formed radiopaque elastomer material to align and correlate data obtained from scanning done of a patient's anatomy to create a virtual representation of the scanned portion of the patient's anatomy.

2. The process of claim 1 wherein the first scan of the patient's mouth is done with the mouth at maximum intercuspation.

3. The process of claim 1 further comprising a step of taking a second scan of the patient's mouth at full occlusion position without the formed radiopaque elastomer material being located within a patient's mouth.

4. The process of claim 3 further comprising a step of identifying one or more portions of data obtained from scanning done of the patient's anatomy as being scan distortions and scatter data based on a comparison of the virtual representation of the formed radiopaque elastomer material with a virtual representation made from the second scan.

5. The process of claim 1 further comprising a step of using the virtual representation of the formed radiopaque elastomer material to eliminate scatter effect and background noise from data obtained from the scanning of a patient's anatomy for the formation of the virtual representation of the scanned portion of the patient's anatomy.

6. The process of claim 1 further comprising a step of using the virtual representation of the formed radiopaque elastomer material to prevent scan distortions and scattered data from being incorporated into a scan-based formation of an anatomical representation of a scanned portion of the patient's mouth.

7. The process of claim 1 further comprising a step of using the virtual representation of the formed radiopaque elastomer material to check teeth-to-teeth alignments of the virtual representation of the scanned portion of the patient's anatomy.

8. The process of claim 3 further comprising a step of using the virtual representation of the formed radiopaque elastomer material to check tissue-to-tissue alignments of the first scan and second scan being used to create the virtual representation of the scanned portion of the patient's anatomy.

9. The process of claim 1 further comprising a step of identifying from the scanning being used to form the virtual representation of the scanned portion of the patient's anatomy, a scan whose alignments does not meet one or more parameters as established by the virtual representation of the formed radiopaque elastomer material for use in the creation of a proper virtual representation of the patient's true anatomy.

10. The process of claim 3 wherein the second scan is a scan of an object that is formed from making an impression of a portion of the patient's mouth.

11. The process of claim 3 wherein the second scan is taken outside of the patient's mouth of a combination of dental castings and the formed radiopaque elastomer material, wherein the formed radiopaque elastomer material assists in holding the dental castings in full occlusion.

12. The process of claim 1 further comprising a step of using the virtual representation of the scanned portion of the patient's anatomy to create an implant or an abutment or a dental prosthesis or a dental surgical guide or a dental model of the patient's mouth.

13. A method of filtering scan data to create an anatomical representation of a patient's mouth comprising of the following steps but not necessarily in the order shown:
(A) seating only a radiopaque elastomer material between the jaws of a patient's mouth with the patient biting down only upon the radiopaque elastomer material to form the radiopaque elastomer material into a physical record of at least a portion of each of the patient's jaws and the jaws' positions relative to one other when at the full occlusion position;
(B) taking a first scan of the patient's mouth with only the formed radiopaque elastomer material placed between the jaws of the patient's mouth, the jaws of the patient's mouth being at the full occlusion position;
(C) taking a second scan that is different from the first scan;
(D) using data generated by the first and second scans to create a virtual representation of the formed radiopaque elastomer material; and
(E) using the virtual representation of the formed radiopaque elastomer material to align and correlate scanning used to form a virtual representation of the scanned portion of the patient's anatomy.

14. The method of claim 13 wherein the radiopaque elastomer material when seated in the patient's mouth and formed into a physical record is not associated with a bite tray or fiduciary marker or a shape of known dimensions.

15. The method of claim 14 wherein the second scan is taken outside of the patient's mouth and of a casting or an impression made of the patient's mouth.

16. The method of claim 15 wherein the second scan is taken of the casting combined with the formed radiopaque elastomer material.

17. The method of claim 14 further comprising a step of identifying scan distortions and scattered data in data obtained from the scans used to form a virtual representation of the scanned portion of the patient's anatomy by comparing the virtual representation of the formed radiopaque elastomer material with virtual representations made from remaining scans.

18. The method of claim 14 wherein the step of using the virtual representation of the formed radiopaque elastomer material further comprises a step of establishing one or more parameters that are used to determine if the scans properly represent the patient's true dental anatomy.

19. The method of claim 18 wherein the first and second scans have different levels of detail definition of an architecture of the patient's mouth.

20. The method of claim 13 wherein the radiopaque elastomer material is polyvinyl siloxane in 85 Shore A Durometer quality.

* * * * *